(12) United States Patent
Goldberg et al.

(10) Patent No.: US 9,387,061 B2
(45) Date of Patent: *Jul. 12, 2016

(54) PELVIC IMPLANTS AND METHODS OF IMPLANTING THE SAME

(71) Applicant: Boston Scientific Scimed, Inc., Maple Grove, MN (US)

(72) Inventors: Roger Goldberg, Evanston, IL (US); Brent Palmisano, Fiskdale, MA (US); John Sherry, Needham, MA (US); James Goddard, Pepperell, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/570,653

(22) Filed: Dec. 15, 2014

(65) Prior Publication Data
US 2015/0094527 A1     Apr. 2, 2015

Related U.S. Application Data

(63) Continuation of application No. 13/218,840, filed on Aug. 26, 2011, now Pat. No. 8,911,348.

(60) Provisional application No. 61/379,565, filed on Sep. 2, 2010.

(51) Int. Cl.
*A61F 2/00*     (2006.01)
*A61B 17/00*     (2006.01)

(52) U.S. Cl.
CPC ............. *A61F 2/0063* (2013.01); *A61F 2/0045* (2013.01); *A61B 2017/00805* (2013.01)

(58) Field of Classification Search
CPC ... A61F 2/0004; A61F 2/0031; A61F 2/0063; A61F 2/0045
USPC ............... 600/37, 29–32; 623/23.72; 606/151
See application file for complete search history.

(56) References Cited

U.S. PATENT DOCUMENTS

| 669,034 A | 2/1901 | Manly |
|---|---|---|
| 2,687,131 A | 8/1954 | Raiche |

(Continued)

FOREIGN PATENT DOCUMENTS

| DE | 10056169 A1 | 6/2002 |
|---|---|---|
| EP | 0088714 A1 | 9/1983 |

(Continued)

OTHER PUBLICATIONS

Non Final Office Action for U.S. Appl. No. 13/218,840, mailed on Jun. 7, 2013, 11 pages.

(Continued)

*Primary Examiner* — John Lacyk
(74) *Attorney, Agent, or Firm* — Brake Hughes Bellermann LLP (57) ABSTRACT

In one embodiment, an implant is configured to be placed within a body of a patient. The implant includes a support member. The support member is configured to be placed adjacent a vaginal apex of a patient. The support member has a length sufficient to extend the length of the vaginal apex but not of a length sufficient to extend from the vaginal apex to a location between a vagina of the patient and a rectum of the patient. The implant also includes first and second arm members coupled to the support member. The arm members are configured to be coupled to bodily tissue of the patient to help secure the implant within the body of the patient.

20 Claims, 7 Drawing Sheets

(56) References Cited

U.S. PATENT DOCUMENTS

| | | |
|---|---|---|
| 3,123,077 A | 3/1964 | Alcamo |
| 4,083,369 A | 4/1978 | Sinnreich |
| 4,324,331 A | 4/1982 | Ignasiak |
| 4,792,336 A | 12/1988 | Hlavacek et al. |
| 4,919,667 A | 4/1990 | Richmond |
| 4,979,956 A | 12/1990 | Silvestrini |
| 4,998,912 A | 3/1991 | Scarbrough et al. |
| 5,013,292 A | 5/1991 | Lemay |
| 5,082,112 A | 1/1992 | Dunklee |
| 5,112,344 A | 5/1992 | Petros |
| 5,149,329 A | 9/1992 | Richardson |
| 5,217,466 A | 6/1993 | Hasson |
| 5,217,486 A | 6/1993 | Rice et al. |
| 5,217,494 A | 6/1993 | Coggins et al. |
| 5,263,969 A | 11/1993 | Phillips |
| 5,356,432 A | 10/1994 | Rutkow et al. |
| 5,362,294 A | 11/1994 | Seitzinger |
| 5,364,408 A | 11/1994 | Gordon |
| 5,383,905 A | 1/1995 | Golds et al. |
| 5,405,359 A | 4/1995 | Pierce |
| 5,425,747 A | 6/1995 | Brotz |
| 5,451,235 A | 9/1995 | Lock et al. |
| 5,458,609 A | 10/1995 | Gordon et al. |
| 5,458,636 A | 10/1995 | Brancato |
| 5,464,409 A | 11/1995 | Mohajer |
| 5,485,917 A | 1/1996 | Early |
| 5,527,341 A | 6/1996 | Gogolewski et al. |
| 5,534,008 A | 7/1996 | Acksel |
| 5,540,704 A | 7/1996 | Gordon et al. |
| 5,562,689 A | 10/1996 | Green et al. |
| 5,569,283 A | 10/1996 | Green et al. |
| 5,575,800 A | 11/1996 | Gordon |
| 5,578,044 A | 11/1996 | Gordon et al. |
| 5,584,859 A | 12/1996 | Brotz |
| 5,611,515 A | 3/1997 | Benderev et al. |
| 5,643,311 A | 7/1997 | Smith et al. |
| 5,662,664 A | 9/1997 | Gordon et al. |
| 5,683,402 A | 11/1997 | Cosgrove et al. |
| 5,700,272 A | 12/1997 | Gordon et al. |
| 5,702,397 A | 12/1997 | Goble et al. |
| 5,713,910 A | 2/1998 | Gordon et al. |
| 5,720,761 A | 2/1998 | Kaali |
| 5,741,277 A | 4/1998 | Gordon et al. |
| 5,741,279 A | 4/1998 | Gordon et al. |
| 5,741,299 A | 4/1998 | Rudt |
| 5,840,011 A | 11/1998 | Landgrebe et al. |
| 5,871,488 A | 2/1999 | Tovey et al. |
| 5,899,909 A | 5/1999 | Claren et al. |
| 5,922,826 A | 7/1999 | Kuze et al. |
| 5,931,855 A | 8/1999 | Buncke |
| 5,948,001 A | 9/1999 | Larsen |
| 5,976,127 A | 11/1999 | Lax |
| 5,988,549 A | 11/1999 | Hitomi et al. |
| 6,010,447 A | 1/2000 | Kardjian |
| 6,012,580 A | 1/2000 | Peters et al. |
| 6,039,686 A | 3/2000 | Kovac |
| 6,042,534 A | 3/2000 | Gellman et al. |
| 6,042,536 A | 3/2000 | Tihon et al. |
| 6,042,592 A | 3/2000 | Schmitt |
| 6,044,847 A | 4/2000 | Carter et al. |
| 6,048,351 A | 4/2000 | Gordon et al. |
| 6,096,051 A | 8/2000 | Kortenbach et al. |
| 6,102,921 A | 8/2000 | Zhu et al. |
| 6,195,646 B1 | 2/2001 | Grosh et al. |
| 6,197,036 B1 | 3/2001 | Tripp et al. |
| 6,200,330 B1 | 3/2001 | Benderev et al. |
| 6,221,005 B1 | 4/2001 | Bruckner et al. |
| 6,224,616 B1 | 5/2001 | Kugel |
| 6,267,772 B1 | 7/2001 | Mulhauser et al. |
| 6,273,852 B1 | 8/2001 | Lehe et al. |
| 6,306,079 B1 | 10/2001 | Trabucco |
| 6,322,492 B1 | 11/2001 | Kovac |
| 6,328,686 B1 | 12/2001 | Kovac |
| 6,346,111 B1 | 2/2002 | Gordon et al. |
| 6,375,662 B1 | 4/2002 | Schmitt |
| 6,382,214 B1 | 5/2002 | Raz et al. |
| 6,406,423 B1 | 6/2002 | Scetbon |
| 6,454,778 B2 | 9/2002 | Kortenbach |
| 6,478,727 B2 | 11/2002 | Scetbon |
| 6,491,703 B1 | 12/2002 | Ulmsten |
| 6,502,578 B2 | 1/2003 | Raz et al. |
| 6,506,190 B1 | 1/2003 | Walshe |
| 6,530,943 B1 | 3/2003 | Hoeppffner et al. |
| 6,544,273 B1 | 4/2003 | Harari et al. |
| 6,547,800 B2 | 4/2003 | Foerster et al. |
| 6,551,329 B1 | 4/2003 | Kortenbach et al. |
| 6,565,580 B1 | 5/2003 | Beretta |
| 6,575,897 B1 | 6/2003 | Ory et al. |
| 6,575,998 B2 | 6/2003 | Beyar |
| 6,582,443 B2 | 6/2003 | Cabak et al. |
| 6,592,515 B2 | 7/2003 | Thierfelder et al. |
| 6,592,610 B2 | 7/2003 | Beyar |
| 6,595,911 B2 | 7/2003 | LoVuolo |
| 6,596,001 B2 | 7/2003 | Stormby et al. |
| 6,599,235 B2 | 7/2003 | Kovac |
| 6,599,310 B2 | 7/2003 | Leung et al. |
| 6,612,977 B2 | 9/2003 | Staskin et al. |
| 6,638,209 B2 | 10/2003 | Landgrebe |
| 6,638,210 B2 | 10/2003 | Berger |
| 6,638,211 B2 | 10/2003 | Suslian et al. |
| 6,638,284 B1 | 10/2003 | Rousseau et al. |
| 6,641,524 B2 | 11/2003 | Kovac |
| 6,641,525 B2 | 11/2003 | Rocheleau et al. |
| 6,648,899 B2 | 11/2003 | Kalinski et al. |
| 6,648,921 B2 | 11/2003 | Anderson et al. |
| 6,652,450 B2 | 11/2003 | Neisz et al. |
| 6,666,817 B2 | 12/2003 | Li |
| 6,669,706 B2 | 12/2003 | Schmitt et al. |
| 6,669,735 B1 | 12/2003 | Pelissier |
| 6,673,010 B2 | 1/2004 | Skiba et al. |
| 6,691,711 B2 | 2/2004 | Raz et al. |
| 6,695,855 B1 | 2/2004 | Gaston |
| 6,702,827 B1 | 3/2004 | Lund et al. |
| 6,730,110 B1 | 5/2004 | Harari et al. |
| 6,746,455 B2 | 6/2004 | Beyar et al. |
| 6,752,814 B2 | 6/2004 | Gellman et al. |
| 6,755,781 B2 | 6/2004 | Gellman |
| 6,808,487 B2 | 10/2004 | Migliari |
| 6,830,052 B2 | 12/2004 | Carter et al. |
| 6,848,152 B2 | 2/2005 | Genova et al. |
| 6,872,227 B2 | 3/2005 | Sump et al. |
| 6,881,184 B2 | 4/2005 | Zappala |
| 6,890,338 B1 | 5/2005 | Davis et al. |
| 6,908,425 B2 | 6/2005 | Luscombe |
| 6,911,003 B2 | 6/2005 | Anderson et al. |
| 6,911,034 B2 | 6/2005 | Nobles et al. |
| 6,932,759 B2 | 8/2005 | Kammerer et al. |
| 6,936,052 B2 | 8/2005 | Gellman et al. |
| 6,936,054 B2 | 8/2005 | Chu |
| 6,936,952 B2 | 8/2005 | Takamine |
| 6,946,003 B1 | 9/2005 | Wolowacz et al. |
| 6,953,428 B2 | 10/2005 | Gellman et al. |
| 6,960,160 B2 | 11/2005 | Browning |
| 6,971,986 B2 | 12/2005 | Staskin et al. |
| 6,986,780 B2 | 1/2006 | Rudnick et al. |
| 6,991,597 B2 | 1/2006 | Gellman et al. |
| 7,011,688 B2 | 3/2006 | Gryska et al. |
| 7,025,772 B2 | 4/2006 | Gellman et al. |
| 7,048,682 B2 | 5/2006 | Neisz et al. |
| 7,056,333 B2 | 6/2006 | Walshe |
| 7,070,556 B2 | 7/2006 | Anderson et al. |
| 7,070,558 B2 | 7/2006 | Gellman et al. |
| 7,083,568 B2 | 8/2006 | Neisz et al. |
| 7,083,637 B1 | 8/2006 | Tannhauser |
| 7,090,686 B2 | 8/2006 | Nobles et al. |
| 7,094,199 B2 | 8/2006 | Petros et al. |
| 7,112,171 B2 | 9/2006 | Rocheleau et al. |
| 7,112,210 B2 | 9/2006 | Ulmsten et al. |
| 7,122,039 B2 | 10/2006 | Chu |
| 7,131,943 B2 | 11/2006 | Kammerer |
| 7,131,944 B2 | 11/2006 | Jacquetin |
| 7,198,597 B2 | 4/2007 | Siegel et al. |
| 7,204,801 B2 | 4/2007 | Grocela |
| 7,204,802 B2 | 4/2007 | De Leval |

(56) References Cited

U.S. PATENT DOCUMENTS

| | | |
|---|---|---|
| 7,223,229 B2 | 5/2007 | Inman et al. |
| 7,226,407 B2 | 6/2007 | Kammerer et al. |
| 7,226,408 B2 | 6/2007 | Harai et al. |
| 7,229,453 B2 | 6/2007 | Anderson et al. |
| 7,235,043 B2 | 6/2007 | Gellman et al. |
| 7,244,260 B2 | 7/2007 | Koseki |
| 7,244,759 B2 | 7/2007 | Muller et al. |
| 7,267,645 B2 | 9/2007 | Anderson et al. |
| 7,291,104 B2 | 11/2007 | Neisz et al. |
| 7,351,197 B2 | 4/2008 | Montpetit et al. |
| 7,361,138 B2 | 4/2008 | Wagner et al. |
| 7,364,541 B2 | 4/2008 | Chu et al. |
| 7,402,133 B2 | 7/2008 | Chu et al. |
| 7,413,540 B2 | 8/2008 | Gellman et al. |
| 7,527,588 B2 | 5/2009 | Zaddem et al. |
| 7,878,970 B2 | 2/2011 | Goldberg |
| 8,128,552 B2 | 3/2012 | O'Donnell |
| 8,911,348 B2 * | 12/2014 | Goldberg et al. ............... 600/37 |
| 9,078,727 B2 | 7/2015 | Miller |
| 2001/0023356 A1 | 9/2001 | Raz et al. |
| 2001/0049467 A1 | 12/2001 | Lehe et al. |
| 2002/0010457 A1 | 1/2002 | Duchon et al. |
| 2002/0028980 A1 | 3/2002 | Thierfelder et al. |
| 2002/0099259 A1 | 7/2002 | Anderson et al. |
| 2002/0128670 A1 | 9/2002 | Ulmsten et al. |
| 2002/0133236 A1 | 9/2002 | Rousseau |
| 2002/0143234 A1 | 10/2002 | LoVuolo |
| 2002/0147382 A1 | 10/2002 | Neisz et al. |
| 2002/0151909 A1 | 10/2002 | Gellman et al. |
| 2002/0156489 A1 | 10/2002 | Gellman et al. |
| 2003/0009181 A1 | 1/2003 | Gellman et al. |
| 2003/0023138 A1 | 1/2003 | Luscombe |
| 2003/0023250 A1 | 1/2003 | Watschke et al. |
| 2003/0055313 A1 | 3/2003 | Anderson et al. |
| 2003/0078604 A1 | 4/2003 | Walshe |
| 2003/0125715 A1 | 7/2003 | Kuehn et al. |
| 2003/0149334 A1 | 8/2003 | Ulmsten et al. |
| 2003/0176762 A1 | 9/2003 | Kammerer |
| 2003/0191360 A1 | 10/2003 | Browning |
| 2003/0208208 A1 | 11/2003 | Chu |
| 2003/0220538 A1 | 11/2003 | Jacquetin |
| 2003/0225424 A1 | 12/2003 | Benderev |
| 2003/0233107 A1 | 12/2003 | Gellman et al. |
| 2003/0233108 A1 | 12/2003 | Gellman et al. |
| 2004/0006353 A1 | 1/2004 | Bosley, Jr. et al. |
| 2004/0015048 A1 | 1/2004 | Neisz et al. |
| 2004/0015177 A1 | 1/2004 | Chu |
| 2004/0034372 A1 | 2/2004 | Chu |
| 2004/0039246 A1 | 2/2004 | Gellman et al. |
| 2004/0039453 A1 | 2/2004 | Anderson et al. |
| 2004/0059293 A1 | 3/2004 | Chu et al. |
| 2004/0068159 A1 | 4/2004 | Neisz et al. |
| 2004/0073234 A1 | 4/2004 | Chu et al. |
| 2004/0087970 A1 | 5/2004 | Chu et al. |
| 2004/0106847 A1 | 6/2004 | Benderev |
| 2004/0116944 A1 | 6/2004 | Chu et al. |
| 2004/0133217 A1 | 7/2004 | Watschke |
| 2004/0138747 A1 | 7/2004 | Kaladelfos |
| 2004/0181243 A1 | 9/2004 | Chu et al. |
| 2004/0186515 A1 | 9/2004 | Rosenblatt |
| 2004/0225181 A1 | 11/2004 | Chu et al. |
| 2004/0230206 A1 | 11/2004 | Gellman et al. |
| 2004/0231678 A1 | 11/2004 | Fierro |
| 2004/0236356 A1 | 11/2004 | Rioux et al. |
| 2004/0249397 A1 | 12/2004 | Delorme et al. |
| 2004/0249473 A1 | 12/2004 | Delorme et al. |
| 2005/0004427 A1 | 1/2005 | Cervigni |
| 2005/0004576 A1 | 1/2005 | Benderev |
| 2005/0038451 A1 | 2/2005 | Rao et al. |
| 2005/0038452 A1 | 2/2005 | Chu |
| 2005/0075660 A1 | 4/2005 | Chu et al. |
| 2005/0080317 A1 | 4/2005 | Merade |
| 2005/0090706 A1 | 4/2005 | Gellman et al. |
| 2005/0096499 A1 | 5/2005 | Li et al. |
| 2005/0101834 A1 | 5/2005 | Merade |
| 2005/0107805 A1 | 5/2005 | Bouffier et al. |
| 2005/0131391 A1 | 6/2005 | Chu et al. |
| 2005/0131392 A1 | 6/2005 | Chu et al. |
| 2005/0131393 A1 | 6/2005 | Chu et al. |
| 2005/0177022 A1 | 8/2005 | Chu et al. |
| 2005/0192600 A1 | 9/2005 | Nicolo et al. |
| 2005/0222589 A1 | 10/2005 | Chu |
| 2005/0222591 A1 | 10/2005 | Gingras et al. |
| 2005/0234291 A1 | 10/2005 | Gingras |
| 2005/0245787 A1 | 11/2005 | Cox et al. |
| 2005/0250977 A1 | 11/2005 | Montpetit et al. |
| 2005/0250978 A1 | 11/2005 | Kammerer |
| 2005/0256366 A1 | 11/2005 | Chu |
| 2005/0256530 A1 | 11/2005 | Petros |
| 2005/0261545 A1 | 11/2005 | Gellman et al. |
| 2005/0261547 A1 | 11/2005 | Bouffier |
| 2005/0277807 A1 | 12/2005 | MacLean et al. |
| 2005/0278037 A1 | 12/2005 | Delorme et al. |
| 2006/0015001 A1 | 1/2006 | Staskin et al. |
| 2006/0025649 A1 | 2/2006 | Smith et al. |
| 2006/0025783 A1 | 2/2006 | Smith et al. |
| 2006/0041185 A1 | 2/2006 | Browning |
| 2006/0041263 A1 | 2/2006 | Chu et al. |
| 2006/0052801 A1 | 3/2006 | Dreyfuss et al. |
| 2006/0058574 A1 | 3/2006 | Priewe et al. |
| 2006/0058575 A1 | 3/2006 | Zaddem et al. |
| 2006/0069301 A1 | 3/2006 | Neisz et al. |
| 2006/0089524 A1 | 4/2006 | Chu |
| 2006/0089525 A1 | 4/2006 | Mamo et al. |
| 2006/0122457 A1 | 6/2006 | Kovac et al. |
| 2006/0173237 A1 | 8/2006 | Jacquetin |
| 2006/0205995 A1 | 9/2006 | Browning |
| 2006/0211911 A1 | 9/2006 | Jao et al. |
| 2006/0229493 A1 | 10/2006 | Weiser et al. |
| 2006/0229596 A1 | 10/2006 | Weiser et al. |
| 2006/0264698 A1 | 11/2006 | Kondonis et al. |
| 2007/0043255 A1 | 2/2007 | O'Donnell |
| 2007/0055095 A1 | 3/2007 | Chu et al. |
| 2007/0161849 A1 | 7/2007 | Goldberg |
| 2007/0173864 A1 | 7/2007 | Chu |
| 2007/0270890 A1 | 11/2007 | Miller et al. |
| 2007/0276358 A1 | 11/2007 | Barzell et al. |
| 2008/0177132 A1 | 7/2008 | Alinsod et al. |
| 2008/0234543 A1 | 9/2008 | Goldwasser |
| 2009/0171140 A1 | 7/2009 | Chu |
| 2009/0171142 A1 | 7/2009 | Chu |
| 2009/0171143 A1 | 7/2009 | Chu et al. |
| 2010/0152530 A1 | 6/2010 | Timmer et al. |
| 2011/0098527 A1 | 4/2011 | Goldberg |
| 2012/0059217 A1 | 3/2012 | Goldberg |
| 2013/0066145 A1 | 3/2013 | Fairneny et al. |

FOREIGN PATENT DOCUMENTS

| | | |
|---|---|---|
| EP | 0141589 A1 | 5/1985 |
| EP | 0299158 A1 | 1/1989 |
| EP | 0362146 A1 | 4/1990 |
| EP | 0412664 A1 | 2/1991 |
| EP | 0567130 A1 | 10/1993 |
| EP | 0774240 A1 | 5/1997 |
| EP | 1201189 A2 | 5/2002 |
| EP | 1508305 A2 | 2/2005 |
| EP | 1520554 A2 | 4/2005 |
| EP | 1609439 A1 | 12/2005 |
| EP | 1933786 A2 | 6/2008 |
| EP | 2617385 A2 | 7/2013 |
| EP | 1998711 B1 | 12/2013 |
| FR | 2785521 A1 | 5/2000 |
| FR | 2852817 A1 | 10/2004 |
| FR | 2852818 A1 | 10/2004 |
| FR | 2871365 A1 | 12/2005 |
| GB | 670349 | 4/1952 |
| JP | 06114067 A | 4/1994 |
| JP | 08-033635 A | 2/1996 |
| JP | 08117239 A | 5/1996 |
| JP | 2003-523786 A | 8/2003 |
| JP | 2004-524836 A | 8/2004 |
| JP | 2004-526483 A | 9/2004 |
| MX | PA04008407 A | 12/2005 |

(56) References Cited

FOREIGN PATENT DOCUMENTS

| | | | |
|---|---|---|---|
| WO | 96/09796 | A2 | 4/1996 |
| WO | 96/39948 | A1 | 12/1996 |
| WO | 98/35616 | A1 | 8/1998 |
| WO | 98/35632 | A1 | 8/1998 |
| WO | 98/43545 | A1 | 10/1998 |
| WO | 99/37216 | A1 | 7/1999 |
| WO | 00/09039 | A1 | 2/2000 |
| WO | 00/74613 | A | 12/2000 |
| WO | 01/06951 | A | 2/2001 |
| WO | 01/52135 | A1 | 7/2001 |
| WO | 02/31681 | A1 | 4/2002 |
| WO | 02/32284 | A2 | 4/2002 |
| WO | 02/38079 | A2 | 5/2002 |
| WO | 02/058563 | A1 | 8/2002 |
| WO | 02/062237 | A1 | 8/2002 |
| WO | 02/078571 | A2 | 10/2002 |
| WO | 03/068107 | A1 | 8/2003 |
| WO | 03/073960 | A1 | 9/2003 |
| WO | 03/092546 | A2 | 11/2003 |
| WO | 03/096928 | A1 | 11/2003 |
| WO | 03/096929 | A1 | 11/2003 |
| WO | 04/001619 | A1 | 12/2003 |
| WO | 2004/012626 | A1 | 2/2004 |
| WO | 2004/016196 | A2 | 2/2004 |
| WO | 2004/045457 | A1 | 6/2004 |
| WO | 2004/091442 | A2 | 10/2004 |
| WO | 2004/091443 | A2 | 10/2004 |
| WO | 2005/051204 | A1 | 6/2005 |
| WO | 2005/122721 | A2 | 12/2005 |
| WO | 2005/122954 | A1 | 12/2005 |
| WO | 2006/015031 | A2 | 2/2006 |
| WO | 2006/046950 | A1 | 5/2006 |
| WO | 2007/014240 | A1 | 2/2007 |
| WO | 2007/016698 | A2 | 2/2007 |
| WO | 2007/019374 | A2 | 2/2007 |
| WO | 2007/038589 | A2 | 4/2007 |
| WO | 2007/087132 | A1 | 8/2007 |
| WO | 2007/109508 | A1 | 9/2007 |
| WO | 2009/038781 | A1 | 3/2009 |
| WO | 2009/102945 | A2 | 8/2009 |
| WO | 2010/111139 | A2 | 9/2010 |
| WO | 2012/030834 | A2 | 3/2012 |
| WO | 2012/030834 | A3 | 4/2012 |

OTHER PUBLICATIONS

Response to Non Final Office Action for U.S. Appl. No. 13/218,840, filed Sep. 3, 2013, 9 pages.
Final Office Action for U.S. Appl. No. 13/218,840, mailed on Dec. 24, 2013, 11 pages.
Response to Final Office Action for U.S. Appl. No. 13/218,840, filed Mar. 24, 2014, 9 pages.
Notice of Allowance for U.S. Appl. No. 13/218,840, mailed on May 1, 2014, 7 pages.
Non Final Office Action for U.S. Appl. No. 12/983,666, mailed on Oct. 6, 2011, 12 pages.
Response to Non Final Office Action for U.S. Appl. No. 12/983,666, filed Feb. 3, 2012, 9 pages.
Final Office Action for U.S. Appl. No. 12/983,666, mailed on Apr. 24, 2012, 10 pages.
Response to Final Office Action for U.S. Appl. No. 12/983,666, filed Jun. 25, 2012, 8 pages.
Advisory Action for U.S. Appl. No. 12/983,666, mailed on Jul. 13, 2012, 3 pages.
Non Final Office Action for U.S. Appl. No. 12/983,666, mailed on Jul. 30, 2013, 10 pages.
Response to Non Final Office Action for U.S. Appl. No. 12/983,666, filed Oct. 30, 2013, 8 pages.
Final Office Action for U.S. Appl. No. 12/983,666, mailed on May 30, 2014, 13 pages.
Final Office Action for U.S. Appl. No. 11/686,683, mailed on Jan. 19, 2010, 15 pages.
Non Final Office Action for U.S. Appl. No. 11/686,683, mailed on Apr. 26, 2012, 17 pages.
Response to Non Final Office Action for U.S. Appl. No. 11/686,683, filed Aug. 27, 2012, 13 pages.
Final Office Action for U.S. Appl. No. 11/686,683, mailed on Nov. 5, 2012, 26 pages.
Response to Final Office Action for U.S. Appl. No. 11/686,683, filed Feb. 5, 2013, 14 pages.
Non Final Office Action for U.S. Appl. No. 11/686,683, mailed on Aug. 13, 2013, 26 pages.
Response to Non Final Office Action for U.S. Appl. No. 11/686,683, filed Nov. 13, 2013, 13 pages.
Final Office Action for U.S. Appl. No. 11/686,683, mailed on Feb. 25, 2014, 29 pages.
Response to Final Office Action for U.S. Appl. No. 11/686,683, filed May 23, 2014, 12 pages.
Non Final Office Action for U.S. Appl. No. 11/686,683, mailed on Jun. 17, 2014, 31 pages.
Office Action for Japanese Patent Application No. 2009-500607, mailed on Nov. 11, 2011, 3 pages.
Response to Office Action for Japanese Patent Application No. 2009-500607, filed on Feb. 13, 2012, 18 pages.
Office Action for Japanese Patent Application No. 2009-500607, mailed on Jun. 5, 2012, 2 pages.
Notice of Allowance for Japanese Patent Application No. 2009-500607, mailed on Jun. 19, 2013, 3 pages.
Response to Office Action for Japanese Patent Application No. 2012-28740, filed on Aug. 23, 2013, 9 pages.
Office Action for Japanese Patent Application No. 2012-28740, mailed on Dec. 25, 2013, 7 pages.
Advisory Action for U.S. Appl. No. 11/331,777, mailed on Feb. 17, 2010, 3 pages.
Non-Final Office Action for U.S. Appl. No. 11/331,777, mailed on Dec. 6, 2013, 18 pages.
Response to Non-Final Office Action for U.S. Appl. No. 11/331,777, filed Mar. 6, 2014, 8 pages.
Final Office Action for U.S. Appl. No. 11/331,777, mailed on Apr. 14, 2014, 18 pages.
Office Action for U.S. Appl. No. 11/493,148, mailed on Mar. 25, 2010, 14 pages.
Final Office Action for U.S. Appl. No. 11/535,901, mailed on Jan. 29, 2010, 21 pages.
Notice of Allowance for U.S. Appl. No. 11/535,901, mailed on Sep. 21, 2010, 9 pages.
Office Action for Canadian Patent Application No. 2,644,983, mailed on May 26, 2014, 2 pages.
Response to Office Action for Canadian Patent Application No. 2,644,983, filed on Mar. 28, 2014, 28 pages.
Search Report for European Patent Application No. 01117717, mailed on Apr. 18, 2007, 5 pages.
Search Report for European Patent Application No. 05356101, mailed on Nov. 1, 2005, 2 pages.
Office Action for European Patent Application No. 07758616.2, mailed on Jun. 6, 2011, 5 pages.
Search Report or European Patent Application No. EP 90307704, mailed on Apr. 18, 2007, 1 page.
Office Action from European Patent Application No. 06815573.8 mailed on Nov. 15, 2013, 3 pages.
Response to Office Action for EP Patent Application No. 07758616.2 filed on Oct. 17, 2011, 31 pages.
Search report for French Patent Application No. 0303893, mailed on Jan. 21, 2004, 2 pages.
Search report for French Patent Application No. 0303895, mailed on Jan. 21, 2004, 3 pages.
Search report for French Patent Application No. 0406352, mailed on May 25, 2007, 3 pages.
International Search Report for PCT Application No. PCT/AU2004/001674, mailed on Dec. 21, 2004, 3 pages.
International Search Report for PCT Application No. PCT/FR2004/000765, mailed on Dec. 28, 2004, 10 pages.
International Search Report for PCT Application No. PCT/FR2004/000766, mailed on Nov. 8, 2004, 9 pages.

(56) References Cited

OTHER PUBLICATIONS

International Preliminary Report on Patentability for PCT Patent Application No. PCT/US2011/049753 mailed on Mar. 14, 2013, 9 pages.
International Search Report for PCT Patent Application No. PCT/US1998/03066, mailed on May 28, 1998, 2 pages.
International search Report for PCT Patent ApplicationNo. PCT/US2001/031234, mailed on Dec. 14, 2001, 1 page.
International Search Report for PCT Patent Application No. PCT/US2001/30033, mailed on May 10, 2002, 1 page.
International Search Report for PCT Patent Application No. PCT/US2004/035329, mailed on Jul. 6, 2005, 7 pages.
International Search Report for PCT Patent Application No. PCT/US2005/021267, mailed on Nov. 30, 2005, 6 pages.
International Search Report for PCT Patent Application No. PCT/US2006/028963, mailed on Dec. 6, 2006, 3 pages.
International Search Report for PCT Application Patent No. PCT/US2007/000190, mailed on Jul. 3, 2007, 5 pages.
International Preliminary Report on Patentability for PCT Patent Application No. PCT/US2007/000190, mailed on Jul. 24, 2008.
Written Opinion for PCT Patent Application No. PCT/US2007/000190, mailed on Jul. 3, 2007, 9 pages.
International Search Report for PCT Patent Application No. PCT/US2007/064079, mailed on Aug. 28, 2007, 4 pages.
International Search Report and Written Opinion for PCT Patent Application No. PCT/US2010/027985, mailed on Oct. 20, 2010, 9 pages.
International Search Report and Written Opinion for PCT Application PCT/US2011/049753, mailed on Mar. 6, 2012, 21 pages.
"Capio® CL Transvaginal Suture Capturing Device", The Capio CL Transvaginal Suture Capturing Device allows for a transvaginal suture fixation to Cooper's Ligament for Sling Procedures, Boston Scientific, printed on Apr. 7, 2006, 2 pages.
"Capio® CL Transvaginal Suture Capturing Device", Transvaginal Suture Fixation to Cooper's Ligament for Sling Procedures, Boston Scientific, 2000, 4 pages.
"Capio® Open Access and Standard Suture Capturing Devices", Reach, Throw and Capture: One Step. One Device., Boston Scientific, printed on Apr. 7, 2006, 2 pages.
"Capio® RP Suture Device", Boston Scientific, printed on Apr. 7, 2006, 1 page.
"Capio® Suture Capturing Devices", Reach, Throw and Capture: One Step. One Device., Boston Scientific, 2005, 4 pages.
"Capio CL Transvaginal Suture Capturing Device," Designed for Transvaginal Suture Fixation to Cooper's Ligament for Sling Procedures, Boston Scientific, 2000, 1 page.
Hardiman et al, "Sacrospinous Vault Suspension and Abdonimal Colposacropexy: Success Rates and Complications", 8 Section of Urogynecology, Department of Obstetrics and Gynecology, Sep. 18, 1995, 5 pages.
Leron et al., "Sacrohysteropexy with synthetic mesh for the management of uterovaginal prolapse", British Journal of Obstetrics and Gynaecology, 108.3, 2001, pp. 629-633.
Pohl et al., "Bilateral Transvaginal Sacrospinous Colpopexy: Preliminary Experience", 23rd Annual Meeting of the Society of Gynecologic Surgeons, Feb. 24-26, 1997, 7 pages.
Shah et al., "Short-Term Outcome Analysis of Total Pelvic Reconstruction With Mesh: The Vaginal Approach", The Journal of Urology, vol. 171, Jan. 2004, pp. 261-263.
Response to Final Office Action for U.S. Appl. No. 11/686,683, filed Sep. 17, 2014, 13 pages.
Final Office Action for U.S. Appl. No. 11/686,683, mailed on Dec. 23, 2014, 18 pages.
Response to Final Office Action for U.S. Appl. No. 12/983,666, filed Aug. 19, 2014, 8 pages.
Non-Final Office Action for U.S. Appl. No. 12/983,666, mailed on Aug. 26, 2014, 12 pages.
Response to Non-Final Office Action for U.S. Appl. No. 12/983,666, filed Nov. 25, 2014, 9 pages.
Notice of Allowance for U.S. Appl. No. 13/218,840, mailed on Aug. 15, 2014, 7 pages.
Notice of Allowance for U.S. Appl. No. 11/686,683, mailed on Mar. 13, 2015, 7 pages.

* cited by examiner

PELVIC IMPLANTS AND METHODS OF IMPLANTING THE SAME

CROSS-REFERENCE TO RELATED APPLICATIONS

This application is a Continuation of, and claims priority to, U.S. patent application Ser. No. 13/218,840, filed on Aug. 26, 2011, entitled "PELVIC IMPLANTS AND METHODS OF IMPLANTING THE SAME", which, in turn, claims priority to U.S. Patent Application No. 61/379,565, filed on Sep. 2, 2010, entitled "PELVIC IMPLANTS AND METHODS OF IMPLANTING THE SAME," the disclosures of which are incorporated by reference herein in their entirety.

TECHNICAL FIELD

This disclosure relates generally to medical devices and more particularly to implants configured to provide support within a pelvic region of a patient.

BACKGROUND

A variety of medical procedures are performed to treat various female pelvic dysfunctions, including procedures to treat urinary incontinence, and correcting various prolapse conditions such as uterine prolapse, cystoceles, rectoceles, and vaginal vault prolapse.

Women often experience vaginal prolapses due to age or other factors. For example, women may experience a cystocele, a rectocele and/or a hysterocele. A hysterocele occurs when the uterus descends into the vagina, and a rectocele occurs when the rectum bulges into the vagina. Treatments of such dysfunctions have included suturing procedures or the use of implants for support or suspension.

A hysterocele is often treated with a hysterectomy followed by a vaginal vault suspension. Various known devices and procedures are used to deliver and secure pelvic implants within a variety of different anatomical structures within a pelvic region to perform the vaginal vault suspension. Existing implants differ in many ways including size, shape, material, number and location of straps, and in the method in which they are delivered and placed within a pelvic region.

Complications and difficulties may occur during known vaginal vault procedures. Additionally, some known implants may not provide adequate support to the pelvic region. Thus, it would be desirable to provide improved pelvic implants and methods for performing vaginal vault suspension procedures.

SUMMARY

In one embodiment, an implant is configured to be placed within a body of a patient. The implant includes a support member. The support member is configured to be placed adjacent a vaginal apex of a patient. The support member has a length sufficient to extend the length of the vaginal apex but not of a length sufficient to extend from the vaginal apex to a location between a vagina of the patient and a rectum of the patient. The implant also includes first and second arm members coupled to the support member. The arm members are configured to be coupled to bodily tissue of the patient to help secure the implant within the body of the patient.

DETAILED DESCRIPTION

The devices and methods described herein are generally directed to implants and the delivery and placement of such implants within a pelvic region (also referred to herein as "pelvis") of a patient.

Various embodiments of implants are described herein. An implant can be delivered to a pelvic region of a patient using a variety of different delivery devices, only some examples of which are described herein.

Various delivery aids are also described, some of which can be included as part of an implant (e.g., provided to a physician assembled) some of which can be assembled to an implant just prior to implantation. Such delivery aids are typically removed after placing one or more straps of an implant at a desired tissue securement location, leaving the strap to engage the tissue and support the support portion of the implant. For example, a sleeve or dilator assembly can be used to lead an implant or a strap of an implant through a tissue in an intracorporeal location (i.e., within the patient's body), such as the sacrospinous ligament or arcus tendineus. In other embodiments, a sleeve or dilator assembly can be used to lead an implant or a strap of an implant through a tissue and to an extracorporeal location (outside the patient's body), such as through an obturator membrane or muscle and out through an exterior incision in the patient.

As used herein, the terms proximal portion or proximal end refer to the portion or end, respectively, of a device that is closest to a physician when performing a medical procedure, and the terms distal portion or distal end refer to the portion or end, respectively, of the device that is furthest from the physician during a medical procedure. For example, a distal end or portion of a sleeve assembly or dilator device as described herein refers to the end or portion of the device that is first inserted into a body of a patient during a medical procedure. The proximal end or portion is the end or portion of the device that is inserted into a body of the patient after the distal end or distal portion. The terms "trailing end" and "leading end" are also referred to herein and have similar meanings as proximal and distal, respectively. As used herein, the term "leading end" refers to the end of a device or apparatus that is inserted into a body first. The term "trailing end" refers to the end of the device or apparatus that is inserted into the body after the leading end.

Figure 1:
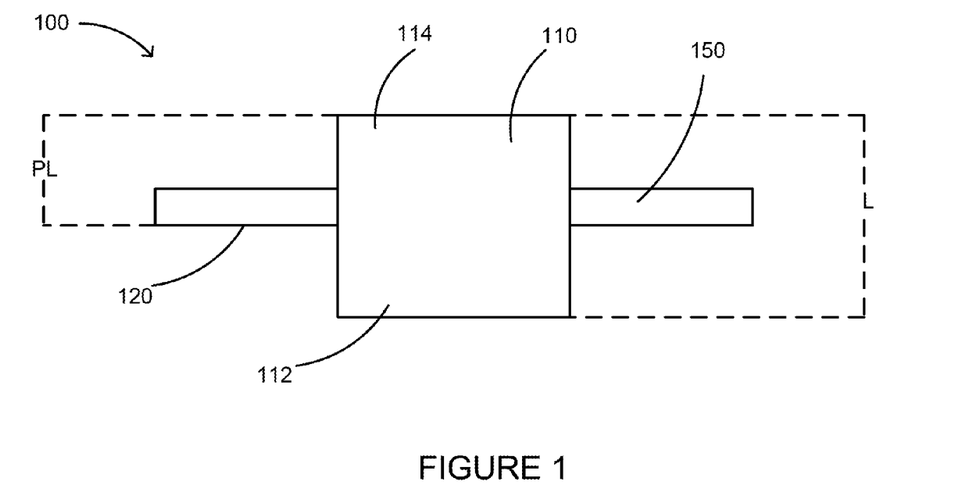
FIG. 1 is a schematic illustration of an implant according to an embodiment of the invention.

FIG. 1 is a schematic illustration of an implant 100 according to an embodiment. The implant 100 includes a support member 110 a first arm member 120 and a second arm member 150. The implant 100 is configured to be placed within a body of a patient and provide support to the body or a portion of the body of the patient.

In the illustrated embodiment, the support member 110 includes an anterior portion 112 and a posterior portion 114. The anterior portion 112 of the support member 110 is configured to be disposed in an anterior compartment of a patient when the implant is placed within the body of the patient. The term "anterior compartment" is used herein to mean an area in the pelvic region located anteriorly of the vaginal apex of the patient (i.e., on the anterior side of the vaginal apex of the patient). In other words, in some embodiments, the anterior compartment is located adjacent an anterior wall of the vagina of the patient.

The posterior portion 112 of the support member 110 is configured to be disposed in posterior compartment of a patient when the implant 100 is placed within the body of the patient. The term "posterior compartment" is used herein to mean an area in the pelvic region located posteriorly of the vaginal apex of the patient (i.e., on the posterior side of the vaginal apex of the patient). In other words, in some embodiments, the posterior compartment is located adjacent a posterior wall of the vagina of the patient.

In some embodiments, the support member 110 is configured to be disposed adjacent to a vaginal apex of the patient when the implant is placed within the body of the patient. Accordingly, in such embodiments, the implant 100 is configured to provide support to the vaginal apex of the patient.

In some embodiments, the support member 110 is configured to be disposed adjacent to a vaginal apex of the patent and is not configured to be disposed between the rectum of the patient and the vagina of the patient. In some embodiments, the support member 110 is configured to span the length of the vaginal apex. Accordingly, in some embodiments, the support member 110 is configured to provide support to the vaginal apex region of the patient but is not configured to provide support to the area adjacent the rectum of the patient. In other words, in such embodiments, the implant 100 is not configured to repair a rectocele. Accordingly, in such embodiments, the implant 100 is not configured to support the rectum or otherwise help prevent the rectum from descending into the vagina of a patient. Additionally, in some embodiments, the implant 100 is not configured to support the bladder of the patient or otherwise prevent the bladder of the patient from descending into the vagina of the patient.

In some embodiments, the support member 110 is of a length L that is sufficient for the support member to be disposed in the anterior compartment of the patient and to be disposed adjacent the vaginal apex of the patient but is insufficient to extend to a location between the rectum of the patient and the vagina of the patient. In other words, the distance between a location in the anterior compartment of a patient and a location between a rectum and a vagina of a patient is greater than then length L of the support member 110. For example, in some embodiments the length of the support member 110 is between 6 and 15 cm. In other embodiments, the length of the support member 110 is less than 6 cm. In yet further embodiments, the length of the support member is greater than 15 cm.

In some embodiments, the posterior portion 114 of the support member 110 is of a length PL that is sufficient to be disposed within the posterior compartment of the patient and adjacent the vaginal apex of the patient but is insufficient to extend to a location between the rectum of the patient and the vagina of the patient. In other words, the distance between the vaginal apex of a patient and a location between a rectum and a vagina of a patient is greater than then length PL of the posterior portion 114 of the support member 110. For example, in some embodiments the length of the posterior portion 114 of the support member 110 is between 3 and 8 cm. In other embodiments, the length of the posterior portion 114 is less than 3 cm. In yet further embodiments, the length of the posterior portion 114 is greater than 8 cm.

The arm members 120 and 150 are coupled to the support member 110 and are configured to be coupled to bodily tissue to help secure the implant 100 in place within the body of the patient. The arm members 120 and 150 can be of any shape or size suitable for extending between the support member 110 and the bodily tissue and coupling to the bodily tissue. Although two arm members are illustrated the implant 100 may include any number of arm members. For example, in some embodiments, the implant 100 includes a single arm member. In other embodiments, the implant 100 includes more than two arm members. In some embodiments, the implant 100 includes exactly two arm members.

In some embodiments, the arm members 120 and 150 are configured to be disposed within and coupled to a sacrospinous ligament of the patient. In other embodiments, the arm members 120 and 150 are configured to be coupled to other bodily tissue.

In some embodiments, the arm members 120 and 150 include tangs configured to help anchor the arm members 120 and 150 within the bodily tissue of the patient. The terms "tanged" or "tangs" as used herein mean roughened or jagged edges or areas, such as can result from cutting a woven or knit mesh material. In other embodiments, the arm members 120 and 150 include barbs, dimples and/or other protrusions configured to engage the bodily tissue of the patient to help retain the implant 100 in place within the body of the patient. In other embodiments, other mechanisms may be used to couple the arm members 120 and 150 to the bodily tissue. For example, in one embodiment the arm members 120 and 150 may be sewn with sutures to the bodily tissue.

The support member 110 and/or the arm members 120 and 150 can each be formed with a mesh material to allow tissue in-growth to the implant 100 after implantation. For example, some or all of the implant 100 can be formed with a mesh material as described in U.S. Patent Pub. 2005/0038452 A1 to Chu, the entirety of which is hereby incorporated by reference. In some embodiments, some or all of an implant 100 can be formed with the Advantage™ Mesh or the Polyform™ Synthetic Mesh material each provided by Boston Scientific Corporation.

The implant 100 can be monolithically formed or alternatively, the implant 100 can be formed with multiple different materials and/or can include multiple different components or portions coupled together. In some embodiments, the implant can be formed with a combination of materials including synthetic and biological materials. For example, the support member 110 can be formed with a first biocompatible material and the arm members 120 and 150 can be formed with a second biocompatible material different than the first material. In other embodiments, the support member 110 is formed with a biological material, and the arm members 120 and 150 are formed with a synthetic material. In some embodiments, the arm members 120 and 150 and the support member 110 have a different weave, knit, pitch, texture, color, and pattern from each other.

In some embodiments, the arm members 120 and 150 are formed monolithically with the support member 110. In other embodiments, the arm members 120 and 150 are formed separate from the support member 110 and can be coupled to the support member 110. In such embodiments, the arm members 120 and 150 and the support member 110 can be coupled in an abutting relationship, an overlapping relationship, or can be bridged. The arm members 120 and 150 can be coupled to the support member by, for example, heat bonding, gluing, using fasteners, and/or sewing. In some embodiments, an arm member can include a heat seal along its length or a portion of its length to help prevent or reduce stretching of the arm member.

The implant 100 may be placed within the body of a patient using a number of different methods. In some embodiments, the implant 100 may be placed within the body of the patient by making a single vaginal incision.

For example, in one embodiment, the implant 100 is placed or implanted within the body of a patient by making an incision in an anterior wall of the vagina. The implant 100 may be inserted into the body of the patient through the anterior vaginal incision. The arm members 120 and 150 may then be coupled to sacrospinous ligaments of the patient. The support member 110 may be positioned within the body of the patient such that the support member 110 is disposed adjacent the vaginal apex of the patient. For example, the support member 110 may be positioned such that the anterior portion 112 of the support member 110 is disposed within an anterior compartment of the patient and the posterior portion 114 of the support member 110 is disposed within a posterior compartment of the patient. In one embodiment, the posterior portion 114 of the support member 110 is positioned within a posterior compartment of the patient through the anterior vaginal incision. In other words, the posterior portion 114 of the support member 110 is positioned without making a second vaginal incision (such as an incision in an anterior wall of the vagina of the patient). In some embodiments, the support member 110 is positioned such that it is disposed adjacent the vaginal apex of the patent, but not disposed between the rectum and vagina of the patient.

In some embodiments, the support member 110 is coupled to the vaginal apex of the patient. For example, in one embodiment, the support member 110 is stitched or sewn to the vaginal apex.

Figure 2:
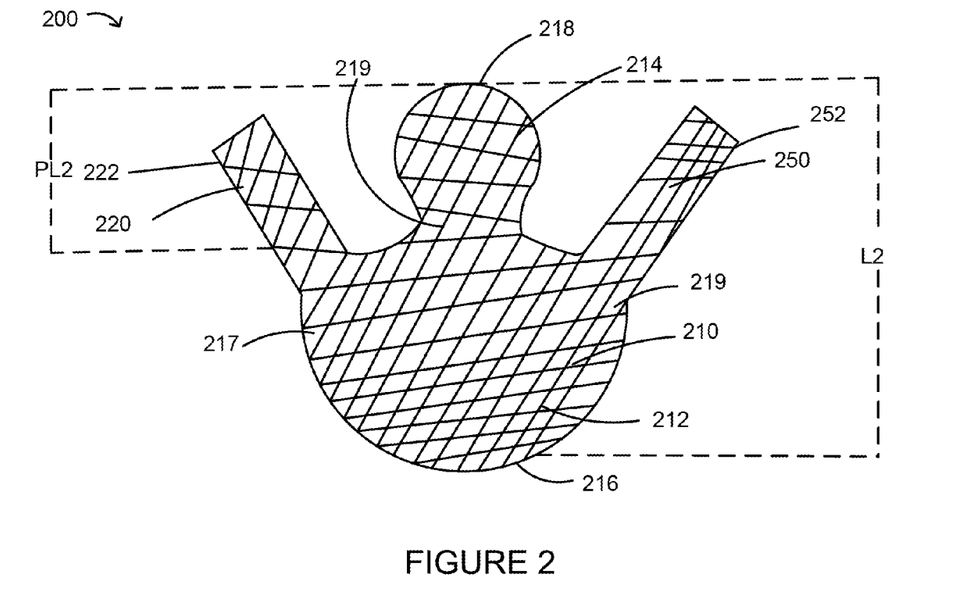
FIG. 2 is a top view of an implant according to an embodiment of the invention.

FIG. 2 is a top view of an implant 200 according to an embodiment. The implant 200 includes a support member 210 a first arm member 220 and a second arm member 250. The implant 200 is configured to be placed within a body of a patient and provide support to the body or a portion of the body of the patient.

In the illustrated embodiment, the support member 210 includes an anterior portion 212 and a posterior portion 214. The anterior portion 212 of the support member 210 is configured to be disposed in an anterior compartment of a patient when the implant is placed within the body of the patient. The posterior portion 212 of the support member 210 is configured to be disposed in posterior compartment of a patient when the implant 200 is placed within the body of the patient.

In the illustrated embodiment, the support member 210 includes end portions 216 and 218. The end portions 216 and 218 each include rounded portions. The support member 210 also includes middle portion 219 that is narrower than the other portions of the support member 210. In some embodiments, the narrow middle portion 219 helps allows the implant 210 to be placed within the body of the patient without folding or kinking.

In the illustrated embodiment, the support member 210 includes side portion 217 and 219. The arm members 210 and 250 extend from the side portions 217 and 219, respectively. In the illustrated embodiments, the arm members 210 and 250 extend from the side portions 217 and 219 and are angled toward the posterior portion 214 of the support member 210.

In the illustrated embodiment, the anterior portion 212 of the support member 210 has a width that is greater than the width of the posterior portion 214 of the support member 210.

In some embodiments, the support member 210 is configured to be disposed adjacent to a vaginal apex of the patient when the implant is placed within the body of the patient. Accordingly, in such embodiments, the implant 200 is configured to provide support to the vaginal apex of the patient.

The support member 210 is configured to be disposed adjacent to a vaginal apex of the patent and not disposed between the rectum of the patient and the vagina of the patient when the support member 210 is placed within the body of the patient. In such embodiments, the support member 210 is configured to provide support to the vaginal apex region of the patient but is not configured to provide support to the area adjacent the rectum of the patient. In other words, in such embodiments, the implant 200 is not configured to be disposed adjacent the rectum or to help repair a rectocele.

The support member 210 is of a length L2 that is sufficient to be disposed in the anterior compartment of the patient and adjacent the vaginal apex of the patient but is insufficient to extend to a location between the rectum of the patient and the vagina of the patient. For example, in the illustrated embodiment, the length of the support member 210 is between 6 and 15 cm. In other words, the distance between a location in the anterior compartment of the patient and a location between a rectum and a vagina of a patient is greater than then length L2 of the support member 210.

The posterior portion 214 of the support member 210 is of a length PL2 that is sufficient to be disposed within the posterior compartment of the patient and adjacent the vaginal apex of the patient but is insufficient to extend to a location between the rectum of the patient and the vagina of the patient. In the illustrated embodiment, the length of the posterior portion 214 of the support member 210 is between 3 and 8 cm. In other words, the distance between the vaginal apex of a patient and a location between a rectum and a vagina of a patient is greater than then length PL2 of the posterior portion 214 of the support member 210.

The arm members 220 and 250 extend from the support member 210 and are configured to be coupled to bodily tissue to help secure the implant 200 in place within the body of the patient. The arm members 220 and 250 can be of any shape or size suitable for extending between the support member 210 and the bodily tissue and coupling to the bodily tissue.

In the illustrated embodiment, the arm members 220 and 250 are configured to be disposed within and coupled to a sacrospinous ligament of the patient. In the illustrated embodiment, the arm members 220 and 250 include tangs 222 and 252, respectively. The tangs 222 and 252 are configured to help anchor the arm members 220 and 250 within the bodily tissue of the patient.

The support member 210 and the arm members 220 and 250 are monolithically formed of a mesh material. The mesh material is configured to allow tissue in-growth to the implant 200 after implantation.

Figure 3:
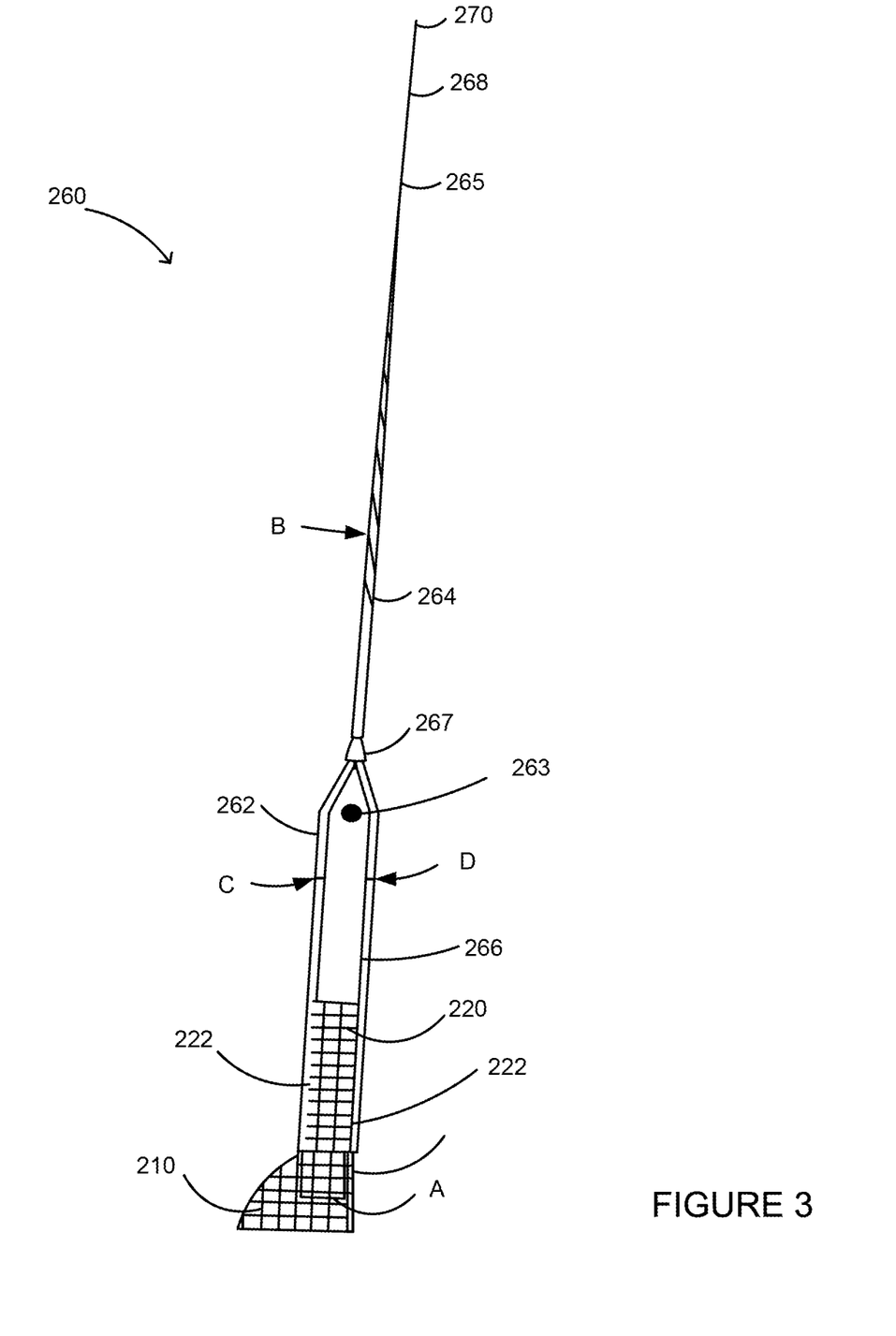
FIG. 3 is a top view of a portion of the implant of FIG. 2 coupled to a delivery assembly.

FIG. 3 is a top view of a portion of the implant 200 coupled to a delivery assembly 260. The delivery assembly 260 is configured to assist in the implantation and placement of the implant 200 within the body of the patient. Although only one delivery assembly is illustrated, it should be understood that a delivery assembly may be associated with each of the arm members of the implant 200.

The delivery assembly includes a sleeve 262 disposed over the arm member 220. A dilator 264 defining a lumen is coupled to the first sleeve 262 by, for example, crimping, heat sealing, stitching, stretching, tip tipping, etc. Alternatively, the sleeve can be formed to include a portion that forms a tapered dilator. The dilator 264 can be used to expand or enlarge a passage during insertion through bodily tissue, to ease the transition to a cross-section or size of the first sleeve 262. In some embodiments, the sleeve 262 is also tapered, which also helps provide a lead-in through the bodily tissue.

The sleeve 262 is secured to the arm member 220 with a suture 266. The suture 266 is looped through the arm member 220. In this embodiment, the suture 266 is weaved or threaded through the arm member 220. For example, as shown in FIG. 3, the suture 266 is weaved through the arm member 220 at location A, as well as other locations along the arm member 220. The threading of the suture 266 through the arm member 220 can also help prevent stretching of the arm member 220 during implantation. The strands of the first suture 266 forming the loop through the arm member 220 extend through an interior lumen (not shown) of the dilator 264 and are crimped closed and heat bonded to an interior wall of the dilator 264 at, for example, a location B shown in FIG. 3, to maintain the arm member 220 within the sleeve 262 and the dilator 264.

The suture 262 can alternatively be coupled to the arm member 220 by, for example, crimping, heat sealing, stitching, stretching, tip tipping, etc. In some embodiments, a suture can be threaded to or secured to the arm member, for example by knotting.

The suture 266 includes a leader portion 268 that extends distally from the leading end 265 of the dilator 264. Alternatively, a separate suture can be coupled to and extend distally from the dilator. A needle 270 is coupled to a distal end of the leader portion 268 of the first suture 266. The needle 268 can be used to associate the implant 200 to a delivery device, as will be described in more detail below.

The sleeve 262 includes a separator 263 disposed between two strands of the suture 266 and near a distal end of the sleeve 262. The separator 263 maintains separation of the strands of the suture 266 within the sleeve 262. The separation of the strands of the suture 266 enables or helps facilitate a cut to be made through only a single strand of the suture 266 at, for example, location C or D, during removal of the sleeve 262 and the delivery assembly 260, as described in more detail below. In the illustrated embodiment, the separator 263 is a seal, which can be formed, for example, by heat stamping two sides of the sleeve 262 together. Other types of separators can alternatively be used, such as for example, a separate component coupled within the sleeve, or an adhesive can be used to couple the two sides of the sleeve together at a location between the strands.

The dilator 264 tapers from a first diameter at a trailing end 267 to a second, smaller diameter at a leading end 265. The first diameter can be, for example, between about 0.2 and 0.5 cm (0.08 to 0.2 inches) and the second diameter can be, for example, between about 0.03 to 0.2 cm (0.01 to 0.08 inches). For example, in some embodiments, the first diameter can be about 0.37 cm (0.15 inches) and the corresponding second diameter can be 0.03 cm (0.01 inches). The dilator 264 can be formed, for example, by molding, extruding, casting, sintering, forging, machining, or other known methods of manufacturing such medical devices.

Figure 4:
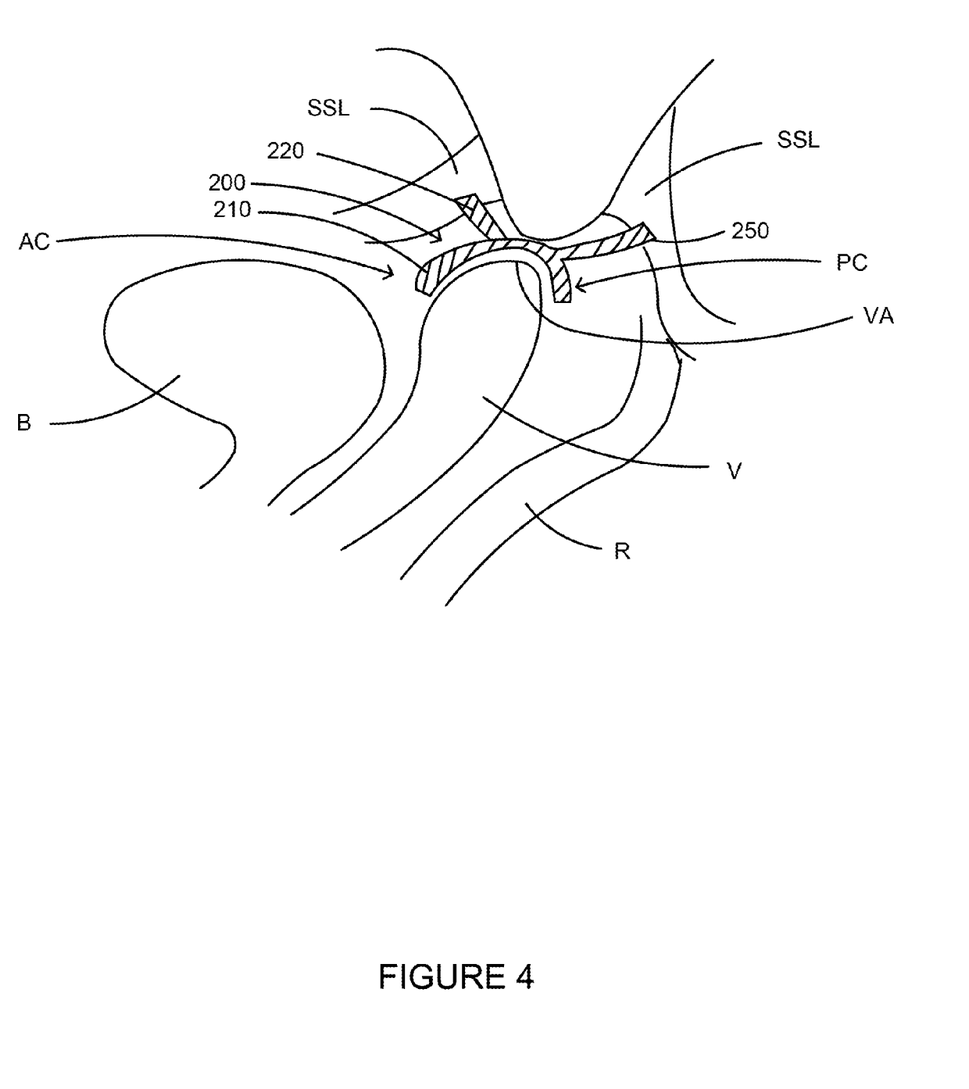
FIG. 4 is a schematic illustration of the implant of FIG. 2 disposed within a body of a patient.

FIG. 4 shows the implant 200 positioned within the pelvic region of a patient. Arm member 220 is coupled to a first portion of the sacrospinous ligament SSL of the patient. Arm member 250 is coupled to a second portion of the sacrospinous ligament SSL of the patient. The support member 210 is disposed adjacent the vaginal apex VA of the patient. The anterior portion 212 of the support member 210 is disposed in the anterior compartment AC of the patient and the posterior portion 214 of the support member 210 is disposed in the posterior compartment PC of the patient. In the illustrated embodiment, the support member 210 does not extend to a location between the rectum R and the vagina V of the patient and is not configured to help repair a rectocele. Additionally, in the illustrated embodiment, the support member 210 does not extend to a location between the bladder B of the patient and the vagina of the patient and is not configured to help repair a cystocele.

In some embodiments, the implant 200 can be delivered into a pelvic region of a patient through a vaginal incision (e.g., a transvaginal approach). An incision can be made, for example, along an anterior vaginal mucosa. The incision can be, for example, 4 cm to 6 cm (1.57 to 2.36 inches) in length and can extend approximately 2 cm to 3 cm (0.79 inches to 1.18 inches) to the meatus. The vaginal epithelium is dissected from the underlying periurethral fascia toward the sacrospinous ligament SSL. Specifically, the anterior vaginal wall is opened and the endopelvic connective tissue is separated from the pubic ramus at the level of the bladder neck to the ischial spine, exposing the paravesical and pararectal space. The sacrospinous ligament SSL is identified and isolated through this defect. The anterior incision to place the implant 200 is about 4 cm long extending about 1 cm from the vaginal apex to the level of the proximal urethra. The incision is also known to be an anterior corporaphy incision. Variations in the incision can depend, for example, on the size of the implant 200, the needed repair or disease state to be treated, and/or the location of the intended placement of the implant 200.

The arm members 220 and 250 of the implant 210 can each be delivered through the sacrospinous ligament SSL using a suturing device. For example, a Capio® suturing device as sold by Boston Scientific may be used. In other embodiments, other suturing devices may be used.

Figure 5:
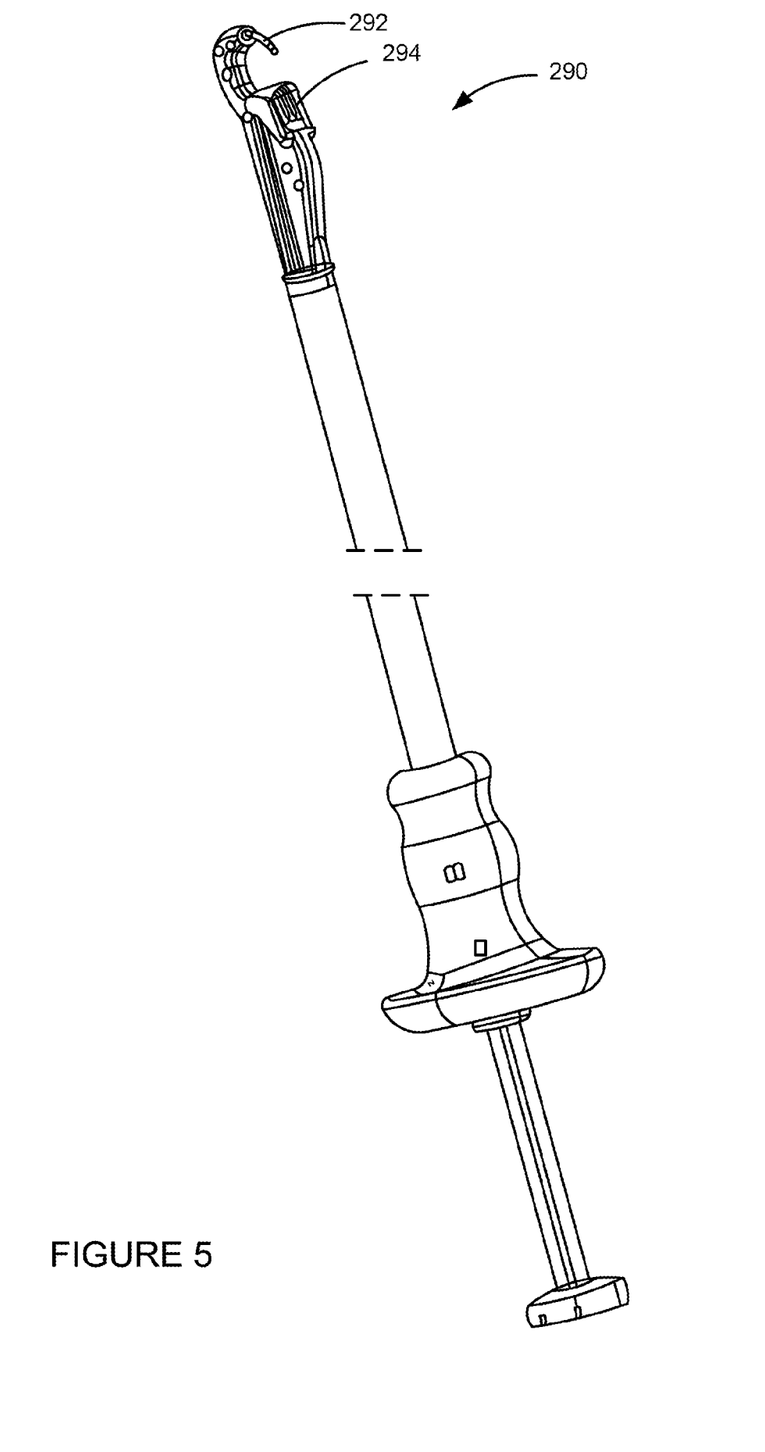
FIG. 5 is a perspective view of an instrument that may be used to deliver the implant of FIG. 2 into the body of a patient.

In the illustrated embodiment, a suturing delivery device 290, as shown in FIG. 5 is used to attach the implant 200 to the bodily tissue. For example, the needle 270 coupled to one arm member 220 is loaded into the carrier 292 (shown partially extended in FIG. 5) of the delivery device 290. The delivery device 290 can then be used to pass the needle 270 and the arm member 220 (with the sleeve 262 and the dilator 264 attached thereto) through the sacrospinous ligament SSL of the patient. Specifically, the carrier 292 of the delivery device 290 is inserted into a body of a patient through the vagina and positioned adjacent the sacrospinous ligament SSL. The carrier 292 is then actuated such that the needle 270 pierces through the sacrospinous ligament SSL. The needle 270 and a distal end of the leader portion 268 of the suture 266 are caught or retrieved by a catch 294 of the delivery device 290 after passing through the sacrospinous ligament SSL. The delivery device 290 is then removed through the vagina, and the needle 270 is removed from the catch 294. The sleeve 262 and the dilator 264 are pulled through the sacrospinous ligament SSL. For example, the user can pull the leader portion 268 of the suture 266 or the dilator 264 through the sacrospinous ligament SSL such that the arm member 220 is disposed within the sacrospinous ligament SSL. This procedure is then repeated to deliver the arm member 250 into the sacrospinous ligament SSL.

After the arm members 220 and 250 are disposed within the sacrospinous ligament SSL the arm members 220 and 250 can be adjusted to position and tension the support member 210 with the body of the patient. Each arm member 220 and 250 can be delivered sequentially using the same delivery device, or separate delivery devices can be used for some or all of the arm members. The arm members 220 and 250 (with sleeves) can be tensioned using visual guidance as the user observes the positioning of the support member 210 for the correct tension through the vaginal incision.

After the arm members 220 and 250 have been placed through the sacrospinous ligament SSL and adjusted as described above, the delivery assemblies can be removed from the arm members 220 and 250. For example, as shown in FIG. 3, to remove the delivery assembly 260 from the arm member 220, a portion of the sleeve 262 and one strand of the loop of the suture 266 within the sleeve 262 can be cut, for example, at location C or D. Since the arm member 220 is coupled to the sleeve 262 via the suture 266, cutting through a portion of the sleeve 262, and one strand of the loop of the suture 266, the sleeve 262 will be freely movable relative to the arm member 220. The sleeve 262 (and dilator 262 which is coupled to the sleeve 262) can then be pulled off of the arm member 220 by pulling on the sleeve 262 and the uncut strand of the suture 266. The cut portion of the suture 266 will also be free to pull through the arm member 220. Thus, the suture 266 remains secured to the sleeve 262 and will simply unravel or unthread itself from the arm member 220. With the sleeve 262 removed from the arm member 220, the tangs 222 on the arm member 220 can engage the surrounding tissue into which the arm member 220 is placed to couple the arm member 220 to the bodily tissue (the sacrospinous ligament).

After the arm members 220 and 250 are secured within the sacrospinous ligament SSL, excess portions of the arm members 220 and 250 can be trimmed as needed. For example, if a portion of the arm member 220 extends through the sacrospinous ligament SSL after the arm members 220 and 250 are placed within the sacrospinous ligament SSL, the portion of the arm member 220 extending through the sacrospinous ligament SSL can be removed.

In other embodiments, the arm members 220 and 250 can be secured within a pelvic region at various different tissue sites. For example, the arm members of the implant can be placed, for example, in a sacrospinous ligament SSL or coccygeus muscle. In other embodiments, the arm members are placed through, endopelvic fascia, or through tissue or ligaments near or in the pubococcygeus muscle, puborectalis muscle, distal tendineus arch of levator ani muscle or other tissue locations within a pelvic region. In still other embodiments, the straps are placed, for example, within an illiococcygeus muscle, or an arcus tendineus.

In some embodiments, a portion of the support member 210 is separately attached to a tissue within the pelvic region. Said another way, a portion of the support member 210 can be secured by means additional to the arm member 220 and 250. For example, a suture can be threaded through the support member 210 and attached to adjacent pelvic tissue, such as the vaginal apex. This can provide additional support for the support member 210.

Figure 6:
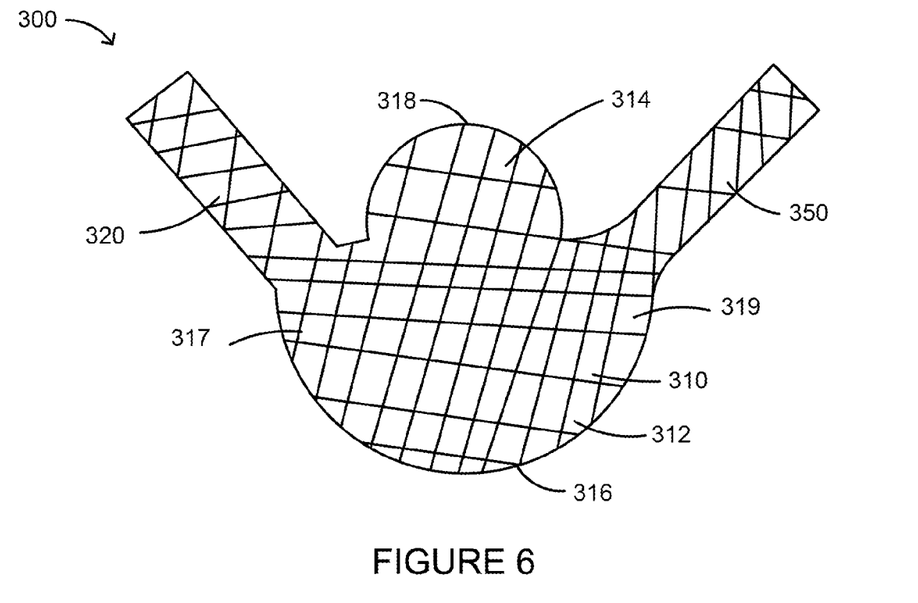
FIGS. 6-8 are top views of implants according to embodiments of the invention.

FIG. 6 is a top view of an implant 300 according to an embodiment. The implant 300 includes a support member 310 a first arm member 320 and a second arm member 350. The implant 300 is configured to be placed within a pelvic region of a patient and provide support to a portion of the body of the patient, such as the vaginal apex of the patient.

In the illustrated embodiment, the support member 310 includes an anterior portion 312 and a posterior portion 314. The anterior portion 312 of the support member 310 is configured to be disposed in an anterior compartment of a patient when the implant is placed within the body of the patient. The posterior portion 312 of the support member 310 is configured to be disposed in posterior compartment of a patient when the implant 300 is placed within the body of the patient.

In the illustrated embodiment, the support member 310 includes end portions 316 and 318. The end portions 316 and 318 each include rounded portions. The support member also includes side portions 317 and 319. The arm members 320 and 350 extend from the side portions 317 and 319, respectively.

Figure 7:
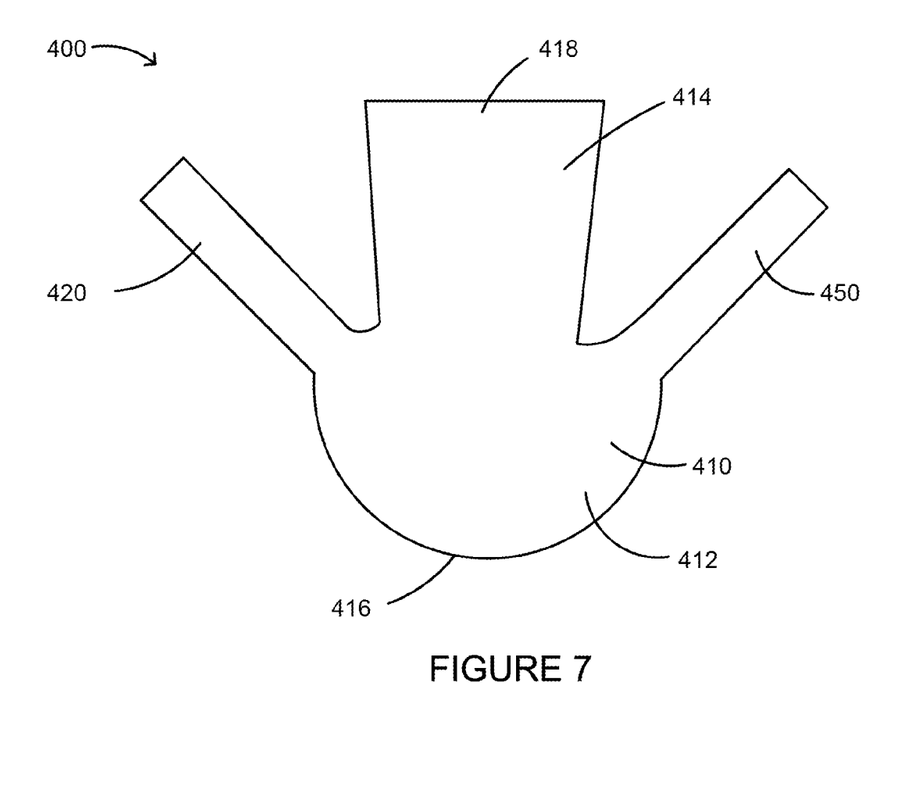

FIG. 7 is a top view of an implant 400 according to an embodiment. The implant 400 includes a support member 410 a first arm member 420 and a second arm member 450. The implant 400 is configured to be placed within a pelvic region of the patient and provide support to a portion of the body of the patient, such as the vaginal apex.

In the illustrated embodiment, the support member 410 includes an anterior portion 412 and a posterior portion 414. The anterior portion 412 of the support member 410 is configured to be disposed in an anterior compartment of a patient when the implant is placed within the body of the patient. The posterior portion 414 of the support member 410 is configured to be disposed in posterior compartment of a patient when the implant 400 is placed within the body of the patient.

The support member 410 includes end portions 416 and 418. End portion 418 includes a linear edge.

Figure 8:
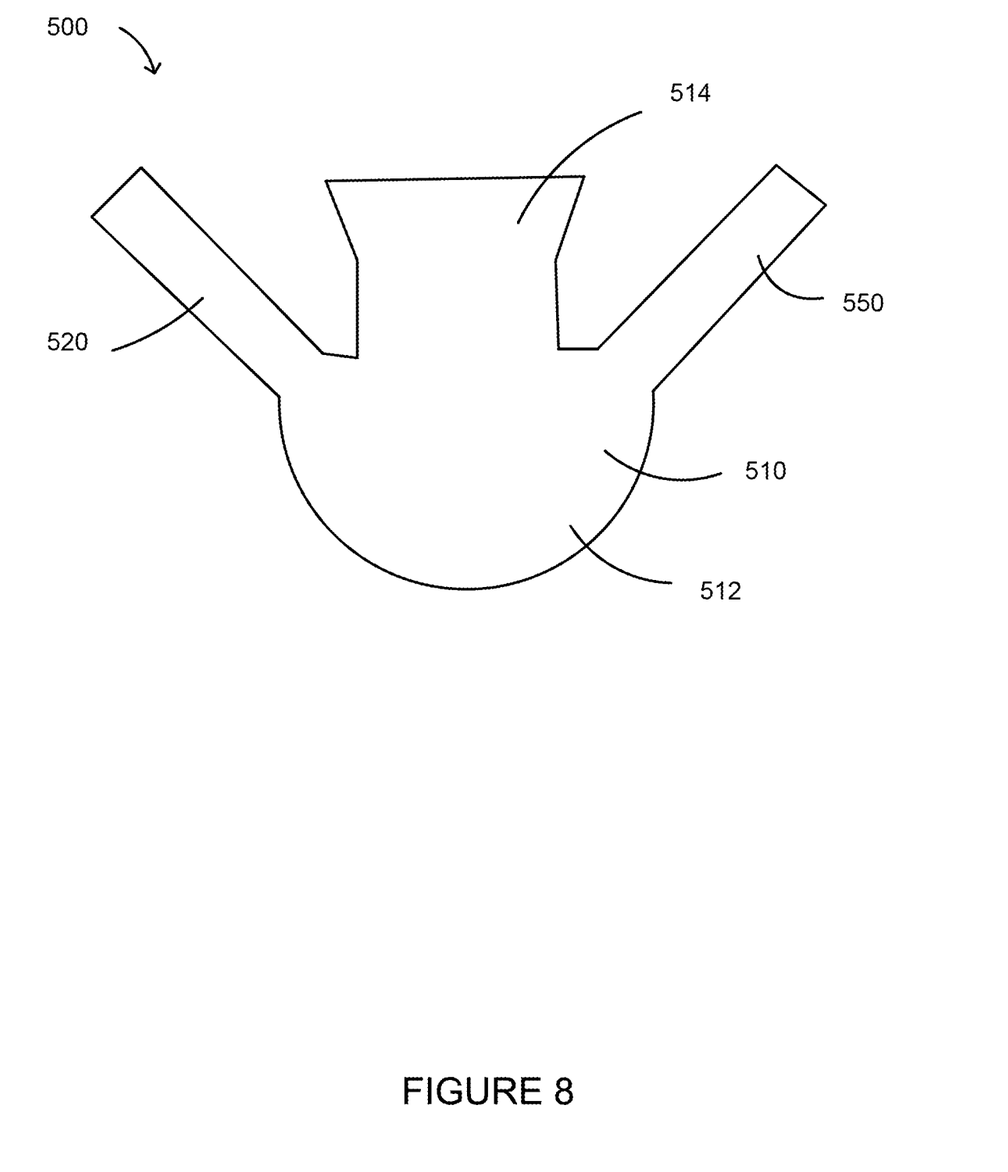

FIG. 8 is a top view of an implant 500 according to an embodiment. The implant 500 includes a support member 510 a first arm member 520 and a second arm member 550. The implant 500 is configured to be placed within a pelvic region of the patient and provide support to a portion of the body of the patient, such as the vaginal apex.

In the illustrated embodiment, the support member 510 includes an anterior portion 512 and a posterior portion 514. The anterior portion 512 of the support member 510 is configured to be disposed in an anterior compartment of a patient when the implant is placed within the body of the patient. The posterior portion 512 of the support member 510 is configured to be disposed in posterior compartment of a patient when the implant 500 is placed within the body of the patient.

Figure 9:
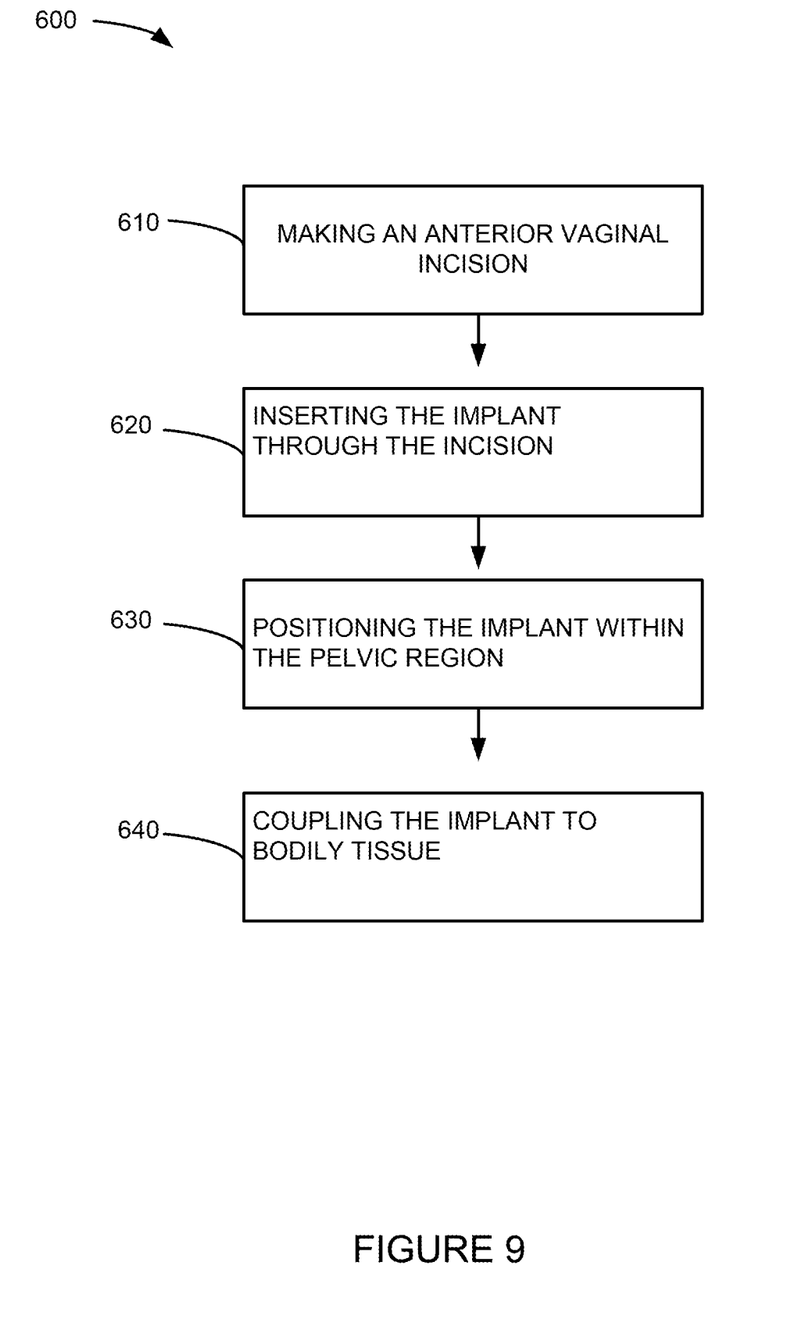
FIG. 9 is a flow chart of a method according to an embodiment of the invention.

FIG. 9 is a flow chart illustrating one method 600 of placing an implant within a pelvic region of a patient. In one embodiment, the method 600 includes at step 610 making an incision in an anterior wall of the vagina of the patient. At step 620, the implant may be inserted into the pelvic region of the patient through the anterior incision.

At step 630, the implant may then be positioned within the pelvic region of the patient. In some embodiments, the implant is positioned such that an anterior portion of the implant is disposed in an anterior compartment of the pelvic region of the patient and a posterior portion of the implant is disposed in a posterior compartment of the pelvic region of the patient. In some embodiments, the implant is positioned such that no portion of the implant is disposed between a rectum of the patient and the vagina of the patient. In some embodiments, the implant is not configured to repair a rectocele (i.e., the implant is not configured to support the rectum of the patient). In some embodiments, the implant is positioned such that no portion of the implant is disposed between the bladder and the vagina. In some embodiments, the implant is not configured to repair a cystocele (i.e., the implant is not configured to support the bladder of the patient). In some embodiments, the implant is positioned through the anterior incision and no additional vaginal incisions are made. In other words, the posterior portion of the implant is positioned in the posterior compartment of the patient by pushing or otherwise placing the posterior portion of the implant into the posterior compartment from the anterior vaginal incision.

At step 640, the implant is coupled to bodily tissue. In some embodiments, arm members of the implant are coupled to sacrospinous ligaments of the patient. In some embodiments, the support member is coupled to bodily tissue, such as by stitching or sewing the support member to the bodily tissue. For example, in some embodiments, arm members of the implant are coupled to the sacrospinous ligament of the patient and the support member is stitched to the vaginal apex of the patient.

In some embodiments, an implant configured to be placed within a body of a patient, comprises a support member, a first arm member, and a second arm member. The support member is configured to be placed adjacent a vaginal apex of a patient. The support member is of a length sufficient to extend the length of the vaginal apex and of a length insufficient to extend from the vaginal apex to a location between a vagina of the patient and a rectum of the patient. The first arm member is coupled to the support member and is configured to be coupled to bodily tissue of the patient to help secure the implant within the body of the patient. The second arm member is coupled to the support member and is configured to be coupled to bodily tissue of the patient to help secure the implant within the body of the patient.

In some embodiments, the first arm member is configured to be coupled to a sacrospinous ligament of the patient. In some embodiments, the first arm member and the second arm member are each configured be coupled to a sacrospinous ligament of the patient. In some embodiments, the support member includes an anterior portion and a posterior portion. The anterior portion is configured to be placed in an anterior compartment of the patient. The posterior portion is configured to be placed in a posterior compartment of the patient.

In some embodiments, the first arm member is formed of a mesh material and includes tangs configured to help secure the arm member to the bodily tissue. In some embodiments, the support member includes a first end and a second end, the first end includes a curved section, the second end includes a curved section. In some embodiments, the support member includes an anterior portion and a posterior portion. The anterior portion has a width that is greater than then width of the posterior portion.

In some embodiments, the support member includes an anterior portion and a posterior portion. The posterior portion has a first portion and a second portion. The first portion is disposed between the second portion and the anterior portion of the support member. The first portion having a width that is shorter than a width of the second portion.

In some embodiments, an implant configured to be placed within a body of a patient, comprises a support member, a first arm member, and a second arm member. The support member is configured to be placed adjacent a vaginal apex of a patient. The support member includes an anterior portion and a posterior portion. The anterior portion is configured to be placed in an anterior compartment of the patient. The posterior portion is configured to be placed in a posterior compartment of the patient. The posterior portion has a length that is shorter than the distance between the vaginal apex and a location between a rectum of the patient and a vagina of the patient. The first arm member is coupled to the support member and is configured to be coupled to bodily tissue of a patient to help secure the implant within the body of the patient. The second arm member is coupled to the support member and is configured to be coupled to bodily tissue of a patient to help secure the implant within the body of the patient.

In some embodiments, the first arm member and the second arm member each extend from a side portion of the support member. In some embodiments, the first arm member is configured to be coupled to a sacrospinous ligament of the patient. In some embodiments, the support member and the first arm member are unitarily formed. In some embodiments, the support member, the first arm member, and the second arm member are unitarily formed of a mesh material.

In some embodiments, a method of placing an implant within a body of a patient, comprises making an incision in an anterior vaginal wall of the patient; inserting the implant through the incision and into an anterior compartment of the patient, the implant including a support member and an arm member, the support member having an anterior portion and a posterior portion; positioning the implant through the incision in the anterior vaginal wall of the patient such that the anterior portion of the support member is disposed in an anterior compartment of the patient and the posterior portion of the support member is disposed in a posterior compartment of the patient and at a location spaced from a rectum of the patient; and coupling the arm member of the implant to a sacrospinous ligament of the patient.

In some embodiments, the method includes associating the arm member with an insertion device. In some embodiments, the positioning includes positioning the implant such that the posterior portion of the support member is disposed within the posterior compartment of the patient without making a posterior vaginal incision. In some embodiments, the positioning includes positioning the support member such that the support member is adjacent a vaginal apex of the patient, but does not extend to a location between a rectum of the patient and a vagina of the patient.

In some embodiments, the coupling includes coupling the arm member to a sacrospinous ligament of the patient. In some embodiments, the method includes coupling the support member to a vaginal apex of the patient. In some embodiments, the arm member is a first arm member, the implant includes a second arm member, and the method further comprises coupling the second arm member to bodily tissue of the patient.

While certain features of the described implementations have been illustrated as described herein, many modifications, substitutions, changes and equivalents will now occur to those skilled in the art. It is, therefore, to be understood that the claims are intended to cover all such modifications and changes as fall within the scope of the embodiments.

What is claimed is:

1. An implant configured to be placed within a body of a patient, comprising:
   a support member, the support member being configured to be placed adjacent a vaginal apex of a patient, the support member being of a length sufficient to extend the length of the vaginal apex but of a length insufficient to extend from the vaginal apex to a location between a vagina of the patient and a rectum of the patient, the support member including a first end and a second end, the first end having a convex curved portion intersecting with a longitudinal axis of the support member;
   a first arm member coupled to the support member and being configured to be coupled to bodily tissue of the patient to help secure the implant within the body of the patient; and
   a second arm member coupled to the support member and being configured to be coupled to bodily tissue of the patient to help secure the implant within the body of the patient.

2. The implant of claim 1, wherein the first arm member is configured to be coupled to a sacrospinous ligament of the patient.

3. The implant of claim 1, wherein the first arm member and the second arm member are each configured be coupled to a sacrospinous ligament of the patient.

4. The implant of claim 1, wherein the support member includes an anterior portion and a posterior portion, the anterior portion is configured to be placed in an anterior compartment of the patient, the posterior portion is configured to be placed in a posterior compartment of the patient.

5. The implant of claim 1, wherein the first arm member is formed of a mesh material and includes tangs configured to help secure the arm member to the bodily tissue.

6. The implant of claim 1, wherein the second end includes a curved section.

7. The implant of claim 1, wherein the support member includes an anterior portion and a posterior portion, the anterior portion having a width that is greater than then width of the posterior portion.

8. The implant of claim 1, wherein the support member includes an anterior portion and a posterior portion, the posterior portion having a first portion and a second portion, the first portion being disposed between the second portion and the anterior portion of the support member, the first portion having a width that is shorter than a width of the second portion.

9. An implant configured to be placed within a body of a patient, comprising:
  a support member, the support member being configured to be placed adjacent a vaginal apex of a patient, the support member including an anterior portion and a posterior portion, the anterior portion being configured to be placed in an anterior compartment of the patient, the posterior portion being configured to be placed in a posterior compartment of the patient, the poster portion having a length that is shorter than the distance between the vaginal apex and a location between a rectum of the patient and a vagina of the patient, the support member including a first end and a second end, the first end having a convex curved portion intersecting with a longitudinal axis of the support member;
  a first arm member coupled to the support member and being configured to be coupled to bodily tissue of a patient to help secure the implant within the body of the patient; and
  a second arm member coupled to the support member and being configured to be coupled to bodily tissue of a patient to help secure the implant within the body of the patient.

10. The implant of claim 9, wherein the first arm member and the second arm member each extend from a side portion of the support member.

11. The implant of claim 9, wherein the first arm member is configured to be coupled to a sacrospinous ligament of the patient.

12. The implant of claim 9, wherein the support member and the first arm member are unitarily formed.

13. The implant of claim 9, wherein the support member, the first arm member, and the second arm member are unitarily formed of a mesh material.

14. A method of placing an implant within a body of a patient, comprising:
  making an incision in an anterior vaginal wall of the patient;
  inserting the implant through the incision and into an anterior compartment of the patient, the implant including a support member and an arm member, the support member having an anterior portion and a posterior portion, the support member including a first end and a second end, the first end having a convex curved portion intersecting with a longitudinal axis of the support member;
  positioning the implant through the incision in the anterior vaginal wall of the patient such that the anterior portion of the support member is disposed in an anterior compartment of the patient and the posterior portion of the support member is disposed in a posterior compartment of the patient and at a location spaced from a rectum of the patient; and
  coupling the arm member of the implant to a sacrospinous ligament of the patient.

15. The method of claim 14, further comprising:
  associating the arm member with an insertion device.

16. The method of claim 14, wherein the positioning includes positioning the implant such that the posterior portion of the support member is disposed within the posterior compartment of the patient without making a posterior vaginal incision.

17. The method of claim 14, wherein the positioning includes positioning the support member such that the support member is adjacent a vaginal apex of the patient, but does not extend to a location between a rectum of the patient and a vagina of the patient.

18. The method of claim 14, wherein the support member and the first arm member are unitarily formed.

19. The method of claim 14, further comprising:
  coupling the support member to a vaginal apex of the patient.

20. The method of claim 14, the arm member being a first arm member, the implant including a second arm member, the method further comprising:
  coupling the second arm member to bodily tissue of the patient.

* * * * *